United States Patent [19]

Riedl et al.

[11] Patent Number: 5,827,857
[45] Date of Patent: Oct. 27, 1998

[54] PYRIDO-FUSED THIENYL- AND FURANYL-OXAZOLIDINONES

[75] Inventors: Bernd Riedl; Dieter Häbich; Andreas Stolle; Martin Ruppelt, all of Wuppertal; Stephan Bartel, Bergisch Gladbach; Walter Guarnieri, Zülpich; Rainer Endermann; Hein-Peter Kroll, both of Wuppertal, all of Germany

[73] Assignee: Bayer Aktiengesellschaft, Leverkusen, Germany

[21] Appl. No.: 781,001

[22] Filed: Jan. 9, 1997

[30] Foreign Application Priority Data

Jan. 16, 1996 [DE] Germany .................. 196 01 264.3

[51] Int. Cl.[6] .................... A61K 31/44; C07D 221/00
[52] U.S. Cl. .................... 514/301; 514/302; 546/112; 546/113; 546/114; 546/115
[58] Field of Search .................... 546/114, 125, 546/209, 115, 112, 113, 135; 514/340, 342, 301, 302; 544/359, 379, 254, 256, 255, 257

[56] References Cited

U.S. PATENT DOCUMENTS

| | | | |
|---|---|---|---|
| 3,998,835 | 12/1976 | Troxier et al. | 260/294.8 C |
| 4,705,799 | 11/1987 | Gregory | 514/376 |
| 4,801,600 | 1/1989 | Wang et al. | 514/376 |
| 4,921,869 | 5/1990 | Wang et al. | 263/24 |
| 4,965,268 | 10/1990 | Wang et al. | 514/253 |
| 5,032,605 | 7/1991 | Wang et al. | 514/376 |
| 5,164,510 | 11/1992 | Brickner | 548/231 |
| 5,254,577 | 10/1993 | Carlson et al. | 514/376 |
| 5,475,014 | 12/1995 | Akasaka et al. | 514/367 |
| 5,561,148 | 10/1996 | Gante et al. | 514/376 |
| 5,574,055 | 11/1996 | Borgulya et al. . | |
| 5,698,574 | 12/1997 | Riedl | 514/376 |

FOREIGN PATENT DOCUMENTS

| | | |
|---|---|---|
| 609905 | 8/1989 | European Pat. Off. . |
| 645376 | 9/1994 | European Pat. Off. . |
| 693491 | 7/1995 | European Pat. Off. . |
| 9308179 | 4/1993 | WIPO . |

*Primary Examiner*—S. Mark Clardy
*Assistant Examiner*—Sabiha N. Qazi
*Attorney, Agent, or Firm*—Sprung Kramer Schaefer & Briscoe

[57] ABSTRACT

The present invention relates to new pyrido-fused thienyl- and furanyl-oxazolidinones, processes for their preparation and their use as medicaments, in particular as antibacterial medicaments.

8 Claims, No Drawings

PYRIDO-FUSED THIENYL- AND FURANYL-OXAZOLIDINONES

The present invention relates to new pyrido-fused thienyl- and furanyl-oxazolidinones, processes for their preparation and their use as medicaments, in particular as antibacterial medicaments.

N-Aryloxazolidinones having antibacterial action are disclosed, for example, in the publications EP 311 090 and U.S. Pat. No. 4,705,799. 3-(Nitrogen-substituted)phenyl-5-beta-amidomethyloxazolidin-2-ones are additionally disclosed in EP 609 905 A1.

Furthermore, oxazolidinone derivatives having a monoamine oxidase inhibitory action are published, inter alia, in WO 93 08 179 A and oxazolidinone derivatives having action as adhesion receptor antagonists are published in EP 645 376.

The present invention relates to pyrido-fused thienyl- and furanyl-oxazolidinones of the general formula (I)

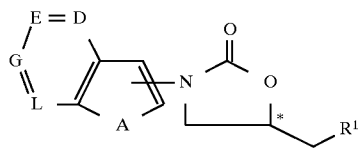

in which
A represents an oxygen or sulphur atom or the $SO_2$ group, and
D, E, G and L are identical or different and at least one of these substituents represents a nitrogen atom and the others represent a radical of the formula $—CR^2$,
in which
$R^2$ denotes hydrogen, cyano, nitro, carboxyl, straight-chain or branched alkyl, acyl or alkoxy each having up to 7 carbon atoms, halogen or a group of the formula $—NR^3R^4$, $—CO—NR^5R^6$, $—NR^5R^6$, $—NR^7—CO—R^8$ or $—S(O)_aR^9$,
in which
$R^3$, $R^4$, $R^5$, $R^6$, $R^7$ and $R^8$ are identical or different and denote hydrogen, phenyl or straight-chain or branched alkyl having up to 6 carbon atoms,
a denotes a number 0, 1 or 2,
$R^9$ denotes phenyl or straight-chain or branched alkyl having up to 4 carbon atoms,
$R^1$ represents azido, hydroxyl or a group of the formula $—OR^{10}$, $O—SO_2R^{11}$ or $—NR^{12}R^{13}$,
in which
$R^{10}$ denotes straight-chain or branched acyl having up to 8 carbon atoms or a hydroxyl protective group,
$R^{11}$ denotes straight-chain or branched alkyl having up to 4 carbon atoms or phenyl which is optionally substituted by straight-chain or branched alkyl having up to 4 carbon atoms,
$R^{12}$ and $R^{13}$ are identical or different and denote cycloalkyl having 3 to 6 carbon atoms, hydrogen, phenyl or straight-chain or branched alkyl or alkoxy each having up to 8 carbon atoms or an amino protective group,
or
$R^{12}$ or $R^{13}$ denotes a group of the formula $—CO—R^{14}$, $—CS—R^{14'}$, $P(O)(OR^{15})(OR^{16})$ or $—SO_2—R^{17}$,
in which
$R^{14}$ and $R^{14'}$ are identical or different and denote cycloalkyl having 3 to 6 carbon atoms, trifluoromethyl, straight-chain or branched alkoxy having up to 8 carbon atoms, phenyl, benzyloxy or hydrogen, or $R^{14}$ and $R^{14'}$ denote straight-chain or branched alkyl having up to 8 carbon atoms, which is optionally substituted by cyano, halogen or trifluoromethyl,
or
denote straight-chain or branched thioalkyl or acyl each having up to 6 carbon atoms,
or
denote a group of the formula $—NR^{18}R^{19}$,
in which
$R^{18}$ and $R^{19}$ are identical or different and denote hydrogen, phenyl or straight-chain or branched alkyl having up to 6 carbon atoms,
or
denote a 5-membered aromatic heterocycle having up to 3 heteroatoms from the series S, N and/or O,
$R^{15}$ and $R^{16}$ are identical or different and denote hydrogen or straight-chain or branched alkyl having up to 4 carbon atoms,
$R^{17}$ denotes straight-chain or branched alkyl having up to 4 carbon atoms or phenyl
and their salts.

Physiologically acceptable salts of the new pyrido-fused thienyl- and furanyl-oxazolidinones can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Salts which may be mentioned are furthermore salts with customary bases, such as, for example, alkali metal salts (e.g. sodium or potassium salts), alkaline earth metal salts (e.g. calcium or magnesium salts) or ammonium salts derived from ammonia or organic amines such as, for example, diethylamine, triethylamine, ethyldiisopropylamine, procaine, dibenzylamine, N-methylmorpholine, dihydroabietylamine, 1-ephenamine or methyl-piperidine.

Reaction products with $C_1$-$C_4$-alkyl halides, in particular $C_1$-$C_4$-alkyl iodides, can additionally function as salts.

Hydroxyl protective group in the context of the definition given above in general represents a protective group from the series: trimethylsilyl, triisopropylsilyl, tert-butyldimethylsilyl, benzyl, benzyloxycarbonyl, 2-nitrobenzyl, 4-nitrobenzyl, tert-butyloxycarbonyl, allyloxycarbonyl, 4-methoxybenzyl, 4-methoxybenzyloxycarbonyl, tetrahydropyranyl, formyl, acetyl, trichloroacetyl, 2,2,2-trichloroethoxycarbonyl, methoxyethoxymethyl, [2-(trimethylsilyl)ethoxy]methyl, benzoyl, 4-methylbenzoyl, 4-nitrobenzoyl, 4-fluorobenzoyl, 4-chlorobenzoyl or 4-methoxybenzoyl. Acetyl, tert-butyldimethylsilyl and tetrahydropyranyl are preferred.

Amino protective groups in the context of the invention are the customary amino protective groups used in peptide chemistry.

These preferably include: benzyloxycarbonyl, 2,4-dimethoxybenzyloxycarbonyl, 4-methoxybenzyloxycarbonyl, methoxycarbonyl, ethoxycarbonyl, tert-butoxycarbonyl, allyloxycarbonyl, phthaloyl, 2,2,2-trichloroethoxycarbonyl, fluorenyl-9-methoxycarbonyl, formyl, acetyl, 2-chloroacetyl, 2,2,2-trifluoroacetyl, 2,2,2-trichloroacetyl, benzoyl, 4-chlorobenzoyl, 4-bromobenzoyl, 4-nitrobenzoyl, phthalimido, isovaleroyl or benzyloxymethylene, 4-nitrobenzyl, 2,4-dinitrobenzyl, 4-nitrophenyl, 4-methoxyphenyl or triphenylmethyl.

The compounds according to the invention can exits in stereoisomeric forms which behave either as image and mirror image (enantiomers), or which do not behave as image and mirror image (diastereomers). The invention relates both to the enantiomers or diastereomers or their respective mixtures. Like the diastereomers, the racemic forms can be separated into the stereoisomerically uniform constituents in a known manner.

Preferred compounds of the general formula (I) are those in which

A represents an oxygen or sulphur atom or the $-SO_2$ group, and

D, E, G and L are identical or different and the least one of these substituents represents a nitrogen atom and the others represent a radical of the formula $-CR^2$,
in which
$R^2$ denotes hydrogen, straight-chain or branched alkyl having up to 6 carbon atoms, fluorine, chlorine or bromine, $R^1$ represents azido, hydroxyl or a group of the formula $-OR^{10}$, $O-SO_2R^{11}$ or $-NR^{13}R^{13}$,
in which
$R^{10}$ denotes straight-chain or branched acyl having up to 6 carbon atoms or benzyl, $R^{11}$ denotes straight-chain or branched alkyl having up to 3 carbon atoms, phenyl or tolyl, $R^{12}$ and $R^{13}$ are identical or different and denote cyclopropyl, cyclopentyl, cyclohexyl, hydrogen, phenyl or straight-chain or branched alkyl or alkoxy each having up to 6 carbon atoms, tert-butoxycarbonyl or benzyloxycarbonyl, or $R^{12}$ or $R^{13}$ denotes a group of the formula $-CO-R^{14}$, $-CS-R^{14'}$, $P(O)(OR^{15})(OR^{16})$ or $-SO_2-R^{17}$,
in which
$R^{14}$ and $R^{14'}$ are identical or different and denote cyclopropyl, cyclobutyl, cyclopentyl, cyclohexyl, trifluoromethyl or straight-chain or branched alkoxy having up to 6 carbon atoms, phenyl, benzyloxy or hydrogen, or $R^{14}$ and $R^{14'}$ denote straight-chain or branched alkyl having up to 6 carbon atoms, which is optionally substituted by cyano, fluorine, chlorine, bromine or trifluoromethyl, or denote straight-chain or branched thioalkyl or acyl each having up to 5 carbon atoms, or denote a group of the formula $-NR^{18}R^{19}$,
in which
$R^{18}$ and $R^{19}$ are identical or different and denote hydrogen, phenyl or straight-chain or branched alkyl having up to 4 carbon atoms, or isoxazolyl, furyl, thienyl, pyrryl, oxazolyl or imidazolyl, $R^{15}$ and $R^{16}$ are identical or different and denote hydrogen or straight-chain or branched alkyl having up to 3 carbon atoms, $R^{17}$ denotes straight-chain or branched alkyl having up to 3 carbon atoms or phenyl and their salts.

Particularly preferred compounds of the general formula (I) are those
in which

A represents an oxygen or sulphur atom or the $-SO_2$ group, and

D, E, G and L are identical or different and at least one of these substituents represents a nitrogen atom and of others represent a radical of the formula $-CR^2$,
in which
$R^2$ denotes hydrogen, straight-chain or branched alkyl having up to 3 carbon atoms or fluorine, $R^1$ represents azido, hydroxyl or a group of the formula $-OR^{10}$, $O-SO-R^{11}$ or $-NR^{12}R^{13}$,
in which
$R^{10}$ denotes straight-chain or branched acyl having up to 5 carbon atoms or benzyl, $R^{11}$ denotes methyl, ethyl, phenyl or tolyl, $R^{12}$ and $R^{13}$ are identical or different and denote cyclopropyl, cyclopentyl, cyclohexyl, hydrogen, phenyl or straight-chain or branched alkyl or alkoxy each having up to 5 carbon atoms, tert-butoxycarbonyl or benzyloxycarbonyl, or $R^{12}$ or $R^{13}$ denotes a group of the formula $-CO-R^{14}$, $-CS-R^{14'}$, $P(O)(OR^{15})(OR^{16})$ or $-SO_2R^{17}$,
in which
$R^{14}$ and $R^{14'}$ are identical or different and denote cyclopropyl, cyclobutyl, cyclopentyl, cyclohexyl, trifluoroethyl or straight-chain or branched alkoxy having up to 5 carbon atoms, phenyl, benzyloxy or hydrogen, or $R^{14}$ and $R^{14'}$ denote straight-chain or branched alkyl having up to 5 carbon atoms, which is optionally substituted by cyano, fluorine, chlorine, bromine or trifluoromethyl, or denote straight-chain or branched thioalkyl or acyl each having up to 4 carbon atoms, or denote a group of the formula $-NR^{18}R^{19}$,
in which
$R^{18}$ and $R^{19}$ are identical or different and denote hydrogen, phenyl or straight-chain or branched alkyl having up to 3 carbon atoms, or denote isoxazolyl, furyl, oxazolyl or imidazolyl, $R^{15}$ and $R^{16}$ are identical or different and denote hydrogen, methyl or ethyl, $R^{17}$ denotes methyl or phenyl and their salts.

Very particularly preferred compounds of the general formula (I) according to the invention are those in which the oxazolidinone radical is bonded to the 5-membered ring heterocycle in position 2.

Processes for the preparation of the compounds of the general formula (I) according to the invention have additionally been found, characterized in that

[A] compounds of the general formula (II) or (III)

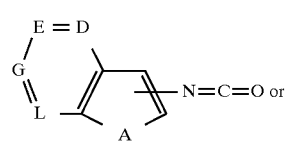

-continued

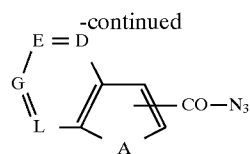

in which

A, D, E, G and L have the meanings indicated above,
are reacted with lithium bromide/$(C_4C_9)_3P(O)$ and epoxides of the general formula (IV)

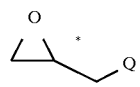  (IV)

in which

Q represents $C_1-C_6$-acyloxy, in inert solvents, if appropriate in the presence of a base, and if $R^1$=OH the hydroxyl function is liberated by a typical ester hydrolysis or by a typical transesterification, or

[B] compounds of the general formula (V)

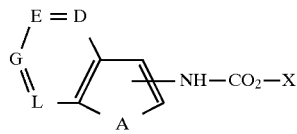  (V)

in which

A, D, E, G and L have the meaning indicated above and

X represents a typical protective group, preferably benzyl, are reacted in inert solvents and in the presence of a base, for example lithium alkyls or lithium N-alkyl- or lithium N-silylalkylamides, preferably N-butyllithium, with epoxides of the general formula (IV), or

[C] if $R^1$=OH, compounds of the general formula (III) are first converted by elimination of nitrogen in alcohols into the compounds of the general formula (Va)

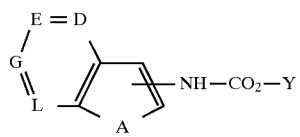  (Va)

in which

A, D, E, G and L have the meaning indicated above and

Y represents straight-chain or branched $C_2-C_6$-alkyl, preferably n-butyl, and these are reacted in a second step with epoxides of the general formula (IV) as described under [A] in inert solvents and in the presence of a base, preferably lithium N-alkyl- or N-silylalkylamides or n-butyllithium, or

[D] compounds of the general formula (VI)

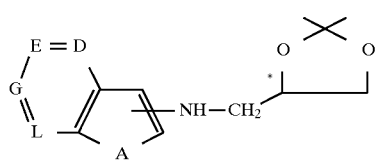  (VI)

in which

A, D, E, G and L have the meaning indicated above,
are reacted either directly with acids and diethyl carbonate, or, by reaction of the compounds of the general formula (VI) with acids the compounds of the general formula (VII)

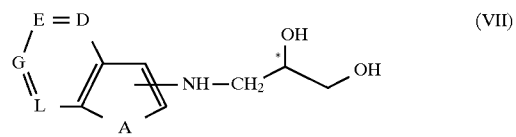  (VII)

in which

A, D, E, G and L have the meaning indicated above,
are first prepared, and these are then cyclized in inert solvents in the presence of an auxiliary, or

[E] compounds of the general formula (Ia)

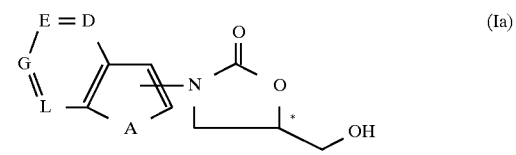  (Ia)

in which

A, D, E, G and L have the meaning indicated above,
are first converted by reaction with $(C_1-C_4)$-alkyl- or phenylsulphonyl chlorides, which are optionally appropriately substituted, in inert solvents and in the presence of a base into the corresponding compounds of the general formula (Ib)

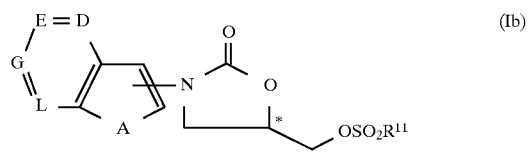  (Ib)

in which

A, D, E, G, L and $R^{11}$ have the meaning indicated above,
then using sodium azide in inert solvents the azides of the general formula (Ic)

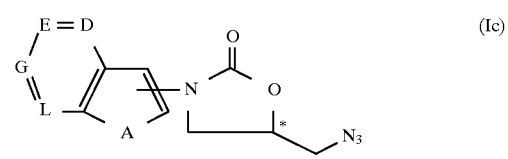  (Ic)

in which

A, D, E, G and L have the meaning indicated above,
are prepared, these are converted in a further step by reaction with $(C_1-C_4-O)_3$-P or $PPh_3$, preferably $(CH_3O)_3P$, in inert solvents and with acids into the amines of the general formula (Id)

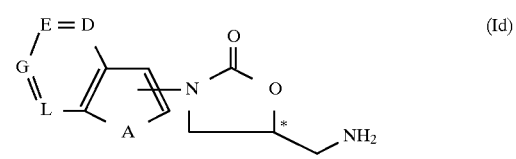  (Id)

in which

A, D, E, G and L have the meaning indicated above, and by reaction with acetic anhydride or other acylating agents of the general formula (VIII)

$$R^{20}\text{—CO—}R^{14} \quad (VIII)$$

in which
$R^{14}$ has the meaning indicated above
and
$R^{20}$ represents halogen, preferably chlorine or the radical —$OCOR^{14}$,
in inert solvents the compounds of the general formula (Ie)

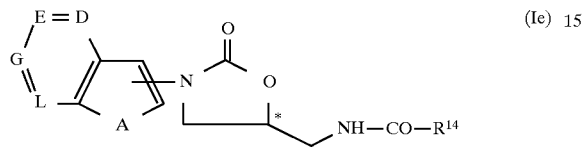

in which

A, D, E, G, L and $R^{14}$ have the meaning indicated above, are prepared, and if $R^1=NR^{12}\text{—CS—}R^{14'}$, compounds of the general formula (Id) are reacted with ethyl dithiocarboxylates and triethylamine and, if $R^1=NR^{12}\text{—CS—}NR^{18}R^{19}$, with thioisocyanates, and in the case of the S-oxides, an oxidation is carried out according to a customary method, and if appropriate further substituents or functional groups already present are introduced or derivatized according to customary methods, such as, for example, alkylation, redox reactions, substitution reactions and/or hydrolyses or incorporation and degradation of protective groups.

The processes according to the invention can be illustrated by way of example by the following reaction schemes:

[A]

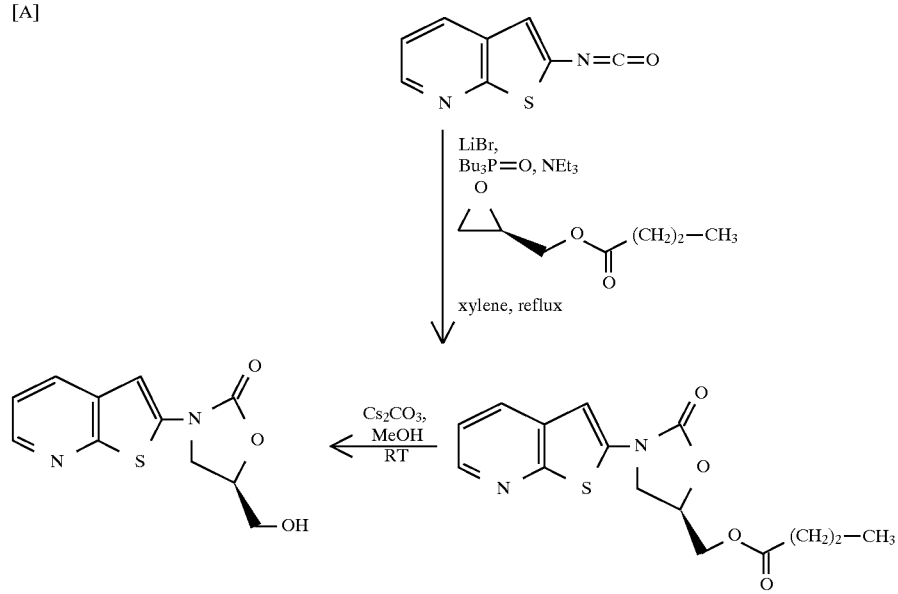

[B]

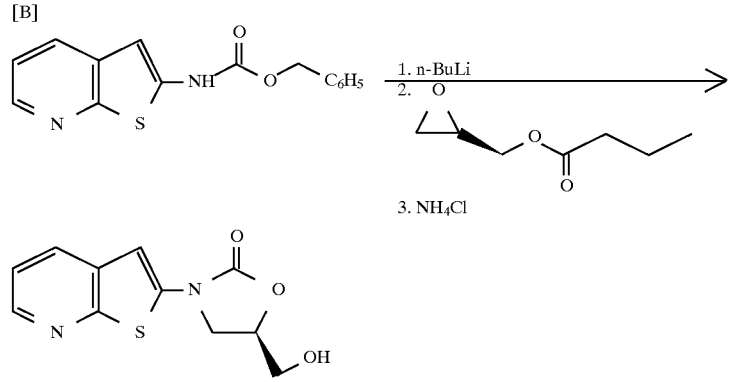

[C] 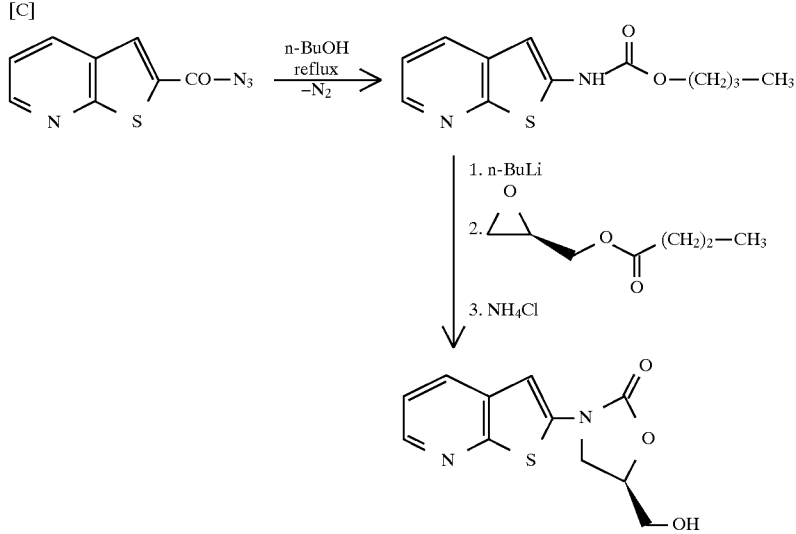
[D] 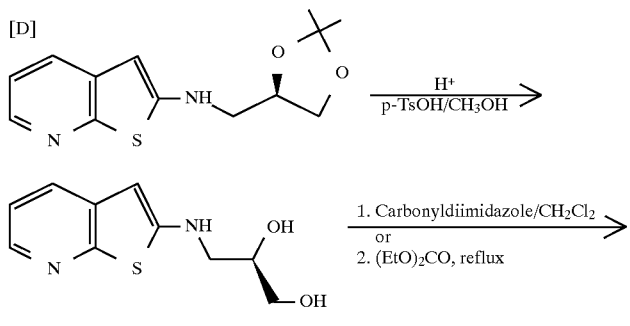
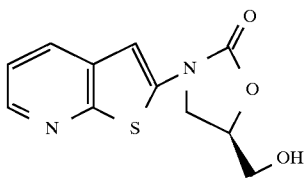
[E] 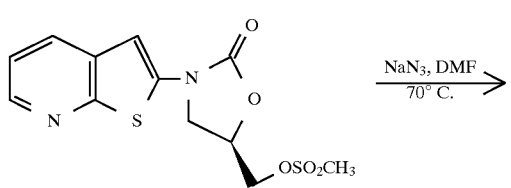
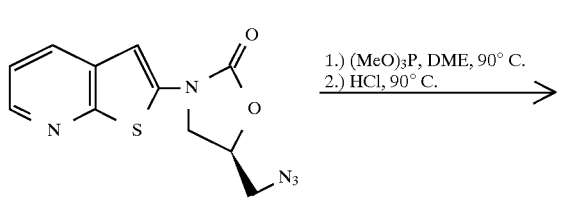

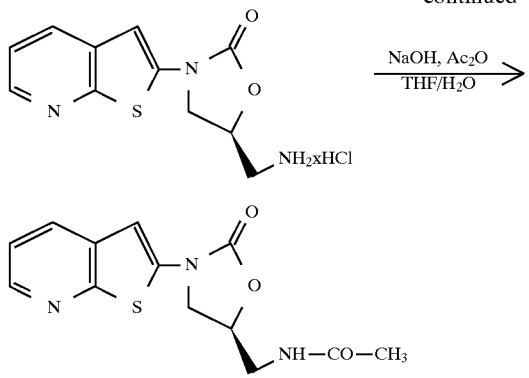

Depending on the individual process steps, suitable solvents are the customary solvents which do not change under the reaction conditions. These preferably include alcohols such as methanol, ethanol, propanol or isopropanol, or ethers such as diethyl ether, dioxane, 1,2-dimethoxyethane, tetrahydrofuran, glycol dimethyl ether or tert-butyl methyl ether, or ketones such as acetone or butanone, or amides such as dimethylformamide or hexamethyl-phosphoramide, or hydrocarbons such as hexane, benzene, dichlorobenzene, xylene or toluene, or dimethyl sulphoxide, acetonitrile, ethyl acetate, or halogenohydrocarbons such as methylene chloride, chloroform or carbon tetrachloride, or pyridine, picoline or N-methylpiperidine. Mixtures of the solvents mentioned can also be used.

Depending on the individual process steps, suitable bases are the customary inorganic or organic bases. These preferably include alkali metal hydroxides such as, for example, sodium or potassium hydroxide, or alkali metal carbonates such as sodium or potassium carbonate, or alkali metal alkoxides such as, for example, sodium or potassium methoxide, or sodium or potassium ethoxide, or organic amines such as ethyldiisopropylamine, triethylamine, picoline, pyridines or N-methylpiperidine, or amides such as sodium amide or lithium diisopropylamide, or lithium N-silylalkylamides, such as, for example, lithium N-(bis) triphenylsilylamide or lithium alkyls such as n-butyllithium.

The base is employed in an amount of from 1 mol to 10 mol, preferably from 1 mol to 3 mol, relative to 1 mol of the compounds of the general formulae (II), (III), (IV) and (Va).

All reactions are in general carried out at normal, elevated or at reduced pressure (e.g. 0.5 to 5 bar). In general, the reactions are carried out at normal pressure.

Process [A] is preferably carried out in xylene or dichlorobenzene, if appropriate in the presence of triethylamine, under reflux.

The base-catalyzed transesterification is carried out using one of the abovementioned alcohols, preferably methanol, in a temperature range from −10° C. to +40° C., preferably at room temperature.

Suitable bases are in general sodium hydrogen carbonate, sodium methoxide, hydrazine hydrate, potassium carbonate or caesium carbonate. Caesium carbonate is preferred.

Process [B] is carried out in one of the abovementioned ethers using lithium alkyl compounds or lithium N-silylamides, such as, for example, n-butyllithium, lithium diisopropylamide or lithium bistrimethylsilylamide, preferably in tetrahydrofuran and lithium bis-trimethylsilylamide or n-butyllithium, in a temperature range from −100° C. to +20° C., preferably from −75° C. to −40° C.

For process [C], suitable alcohols for the 1st step are preferably those mentioned above, in the case of subsequent cyclization tetrahydrofuran.

Suitable bases for the cyclization are preferably the abovementioned lithium N-silylalkyl compounds or n-butyllithium, n-Butyllithium is particularly preferred.

The first reaction step is carried out at the boiling point of the appropriate alcohol and the cyclization is carried out in a temperature range from −70° C. to room temperature.

The cyclization [D] is carried out in the presence of an auxiliary and/or the presence of an acid.

Suitable acids are in general inorganic acids such as, for example, hydrochloric acid or sulphuric acid, or organic carboxylic acids having 1–6C atoms, optionally substituted by fluorine, chlorine and/or bromine, such as, for example, acetic acid, trifluoroacetic acid, trichloroacetic acid or propionic acid, or sulphonic acids having $C_1$-$C_4$-alkyl radicals or aryl radicals such as, for example, methanesulphonic acid, ethanesulphonic acid, benzenesulphonic acid or toluenesulphonic acid. Hydrochloric acid is particularly preferred.

The acid is employed in an amount of from 1 mol to 10 mol, preferably from 1 mol to 2 mol, relative to 1 mol of the compounds of the general formula (VI).

Suitable auxiliaries are the customary reagents such as phosgene, carbonyldiimidazole or diethyl carbonate or trichloromethyl chloroformate. Carbonyldiimidazole, diethyl carbonate and trichloromethyl chloroformate are preferred.

Suitable solvents are the abovementioned halogenohydrocarbons. Methylene chloride is preferred.

The cyclizations are in general carried out in a temperature range from −20 ° C. to 100° C., preferably at −20° C. to room temperature.

The acylation [E] is in general carried out in one of the abovementioned ethers or halogenohydrocarbons, preferably tetrahydrofuran or methylene chloride, in a temperature range from −30° C. to 50° C., preferably from −10° C. to room temperature.

The reductions are in general carried out using hydrides in inert solvents or using boranes, diboranes or complex compounds thereof.

The reductions can in general be carried out by means of hydrogen in water or in inert organic solvents such as alcohols, ethers or halogenohydrocarbons, or mixtures thereof with catalysts such as Raney nickel, palladium, palladium on animal carbon or platinum, or using hydrides or boranes in inert solvents, if appropriate in the presence of a catalyst.

The reductions are preferably carried out using hydrides, such as complex borohydrides or aluminium hydrides and also boranes. Sodium borohydride, lithium borohydride, sodium cyanoborohydride, lithium aluminium hydride, sodium bis-(2-methoxyethoxy)-aluminium hydride or borane-tetrahydrofuran are particularly preferably employed here.

The reduction of the azides [E] is carried out using $(CH_3O)_3P$ and hydrochloric acid.

The reduction is in general carried out in a temperature range from −50° C. to the respective boiling point of the solvent, preferably from −20° C. to +90° C.

Suitable solvents in this context are all inert organic solvents which do not change under the reaction conditions. These preferably include alcohols such as methanol, ethanol, propanol or isopropanol, or ethers such as diethyl ether, dioxane, tetrahydrofuran, glycol dimethyl ether, or diethylene glycol dimethyl ether or amides such as hexamethylphosphoramide or dimethylformamide, or acetic acid. It is also possible to use mixtures of the solvents mentioned.

The hydroxyl protective groups are in general removed according to a customary method, for example by hydrogenolytic cleavage of the benzyl ethers in the abovementioned inert solvents in the presence of a catalyst using hydrogen gas.

The amino protective group is in general also removed by customary methods, namely Boc is preferably removed using hydrochloric acid in dioxane, Fmos using piperidine and Z using HBr/HOAc or by hydrogenolysis.

Redox reactions, reductive amination, transesterification and the halogenation of methyl groups using N-bromosuccinimide (NBS) or N-chlorosuccinimide (NCS) are preferably mentioned, which are illustrated by way of example below.

Suitable solvents for the alkylation are customary organic solvents which do not change under the reaction conditions. These preferably include ethers such as diethyl ether, dioxane, tetrahydrofuran, glycol dimethyl ether, or hydrocarbons such as benzene, toluene, xylene, hexane, cyclohexane or petroleum fractions, or halogenohydrocarbons such as dichloromethane, trichloromethane, tetrachloromethane, dichloroethylene, trichloroethylene or chlorobenzene, or ethyl acetate, or triethylamine, pyridine, dimethyl sulphoxide, dimethylformamide, acetonitrile, acetone nitromethane. It is also possible to use mixtures of the solvents mentioned. Dichloromethane, dimethyl sulphoxide and dimethylformamide are preferred.

The alkylation is carried out in the abovementioned solvents at temperatures from 0° C. to +150° C., preferably at room temperature to +100° C., at normal pressure.

The amidation and the sulphoamidation are in general carried out in inert solvents in the presence of a base and of a dehydrating agent.

Suitable solvents in this context are inert organic solvents which do not change under the reaction conditions. These include halogenohydrocarbons such as dichloromethane, trichloromethane, tetrachloromethane, 1,2-dichloroethane, trichloroethane, tetrachloroethane, 1,2-dichloroethylene or trichloroethylene, hydrocarbons such as benzene, xylene, toluene, hexane, cyclohexane or petroleum fractions, nitromethane, dimethylformamide, acetonitrile or tetrahydrofuran. It is also possible to employ mixtures of the solvents. Dichloromethane and tetrahydrofuran are particularly preferred.

Suitable bases for the amidation and the sulphoamidation are the customary basic compounds. These preferably include alkali metal and alkaline earth metal hydroxides such as lithium hydroxide, sodium hydroxide, potassium hydroxide or barium hydroxide, alkali metal hydrides such as sodium hydride, alkali metal or alkaline earth metal carbonates such as sodium carbonate or potassium carbonate, or alkali metal alkoxides such as, for example, sodium methoxide or ethoxide, potassium methoxide or ethoxide or potassium tert-butoxide, or organic amines such as benzyltrimethyl-ammonium hydroxide, tetrabutylammonium hydroxide, pyridine, triethylamine or N-methylpiperidine.

The amidation and the sulphoamidation are in general carried out in a temperature range from 0° C. to 150° C., preferably at 25° C. to 40° C.

The amidation and the sulphoamidation are in general carried out at normal pressure. However, it is also possible to carry out the process at reduced pressure or at elevated pressure (e.g. in a range from 0.5 to 5 bar).

When carrying out the amidation and the sulphoamidation, the base is in general employed in an amount from 1 to 3 mol, preferably from 1 to 1.5 mol, relative to 1 mol of the respective carboxylic acid.

Suitable dehydrating reagents are carbodiimides such as, for example, diisopropylcarbodiimide, dicyclohexylcarbodiimide or N-(3-dimethylaminopropyl)-N'-ethylcarbodiimide hydrochloride or carbonyl compounds such as carbonyldiimidazole or 1,2-oxazolium compounds such as 2-ethyl-5-phenyl-1,2-oxazolium-3-sulphonate or propanephosphonic anhydride or isobutyl chloroformate or benzotriazolyloxy-tris-(dimethylamino)-phosphonium hexafluorophosphate or diphenyl phosphoramidate or methanesulphonyl chloride, if appropriate in the presence of bases such as triethylamine or N-ethylmorpholine or N-methylpiperidine or 4-dimethylaminopyridine.

Suitable bases for the hydrolysis are the customary inorganic bases. These preferably include alkali metal hydroxides or alkaline earth metal hydroxides such as, for example, sodium hydroxide, potassium hydroxide or barium hydroxide, or alkali metal carbonates such as sodium or potassium carbonate or sodium hydrogen carbonate. Sodium hydroxide and potassium hydroxide are particularly preferably employed.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethylformamide or dimethyl sulphoxide. Alcohols such as methanol, ethanol, propanol or isopropanol are particularly preferably used. It is also possible to employ mixtures of the solvents mentioned.

The hydrolysis is in general carried out in a temperature range from 0° C. to +100° C., preferably from +20° C. to +80° C.

In general, the hydrolysis is carried out at normal pressure. However, it is also possible to work at reduced pressure or at elevated pressure (e.g. from 0.5 to 5 bar).

When carrying out the hydrolysis, the base is in general employed in an amount of from 1 to 3 mol, preferably from 1 to 1.5 mol, relative to 1 mol of the ester. Molar amounts of the reactions are particularly preferably used.

The esterification is in general carried out using the appropriate alcohols in the presence of acids, preferably sulphuric acid, in a temperature range from 0° C. to 150° C., preferably from 50° C. to 100° C. and at normal pressure.

The compounds of the general formulae (IV) and (VIII) are known or can be prepared by customary methods.

The compounds of the general formula (VII) are in the main new and can be prepared, for example, as described above.

The compounds of the general formula (II) are known in some cases or are new and can then be prepared, for example, by reacting the appropriate amines with trichloromethyl chloroformate in one of the abovementioned solvents, preferably xylene at reflux temperature.

The compounds of the general formula (III) are known in some cases or are new and can then be prepared, for example, by, starting from the appropriate carboxylic acids, reacting either with isobutyl chloroformate/acetone, sodium azide/water or with diphenylphosphoryl azide/tetrahydrofuran or with xylene or methylene chloride in the presence of one of the bases indicated above, preferably triethylamine, at −10° C. to room temperature.

The compounds of the general formulae (V) and (Va) are known in some cases or are new and can be prepared either by elimination of nitrogen from the appropriate carboxylic acid azides and reaction with the appropriate alcohols or by reaction of the appropriate amines with chloroformic acid esters, preferably benzyl chloroformate in one of the above-mentioned solvents, preferably tetrahydrofuran or dioxane, in a temperature range from −10° C. to 200° C., preferably from 0° C. to 150° C.

The compounds of the general formula (Ia) are new and can be prepared, for example, as described under [A], [B], [D] or [E].

The compounds of the general formulae (Ib), (Ic), (Id) and (Ie) are new and can be prepared as described above.

The compounds of the general formula (VI) are in the main known or are new and can be prepared, for example, by, starting from the free amines (Ia), reacting either with the acetonide of glyceraldehyde in methanol and in the presence of sodium acetate/sodium cyanoborohydride or of sodium borohydride and methanol in a temperature range from −20° C. to +40° C., preferably from −10° C. to 20° C. and at normal pressure.

The minimum inhibitory concentrations (MIC) were determined by the serial dilution method on Iso-Sensitest agar (Oxoid). For each test substance, a number of agar plates were prepared which contained decreasing concentrations of the active compound. The agar plates were inoculated using a multipoint inoculator (Denley). For inoculation, overnight cultures of the pathogenic organisms were used which had been previously diluted such that each inoculation point contained about $10^4$ colony-forming particles. The inoculated agar plates were incubated at 37° C., and the microbial growth was read off after about 20 hours. The MIC ($\mu$g/ml) indicates the lowest active compound concentration at which no growth can be detected using the naked eye.

MICs ($\mu$g/ml)

| Ex.-No. | Staph. 133 | Staph. 48N | Staph. 25701 | Staph. 9TV | E. coli Neumann | Klebs. 57 USA | Psdm. Bonn |
|---|---|---|---|---|---|---|---|
| 12 | 2 | 2 | 2 | 2 | >64 | >64 | >64 |
| 13 | 8 | 8 | 8 | 8 | >64 | >64 | >64 |
| 16 | 4 | 4 | 4 | 4 | >64 | >64 | >64 |
| 18 | 4 | 4 | 2 | 2 | >64 | >64 | >64 |
| 19 | 1 | 1 | 1 | 0.25 | >64 | >64 | >64 |

For rapidly growing mycobacteria the MIC determination was carried out following the method of broth microdilution described by Swenson [cf. J. M. Swenson, C. Thornberry, U. A. Silcox, Rapidly growing mycobacteria. Testing of susceptibility to 34 antimicrobial agents by broth microdilution. Antimicrobial Agents and Chemotherapy Vol. 22, 186–192 (1982)]. A difference from this was the brain-heart extract medium treated with 0.1% by volume of Tween 80.

The mycobacterial strains used were obtained from the DSM (German Collection of Microorganisms, Braunschweig). They were incubated in a humid chamber at 37° C.

The MICs were read off after 2–14 days when the preparation-free controls were cloudy due to growth. The MIC is defined as the lowest preparation concentration which completely inhibits macroscopically visible growth.

MICs ($\mu$g/ml): My cobacterium smegmatis

| Strain: | DSM 43061 | DSM 43465 |
|---|---|---|
| Ex.-No. | | |
| 13 | 16 | 8 |
| 19 | 32 | 16 |
| Isoniazide | 4 | 1 |
| Streptomycin | 4 | 4 |

The compounds of the general formula (I), (Ia), (Ib), (Ic), (Id) and (Ie) according to the invention have, combined with lower toxicity, a broad antibacterial spectrum, especially against gram-positive bacteria, Haemophilus influenzae, anaerobic microorganisms and for rapidly growing mycobacteria. These properties make possible their use as chemotherapeutic active compounds in human and veterinary medicine.

The compounds according to the invention are particularly efficacious against bacteria and bacteria-like microorganisms such as mycoplasma. They are therefore particularly highly suitable for the prophylaxis and chemotherapy of local and systemic infections in human and veterinary medicine which are caused by such pathogenic organisms.

The present invention includes pharmaceutical preparations which, in addition to non-toxic, inert pharmaceutically suitable excipients, contain one or more compounds according to the invention or which consist of one or more active compounds according to the invention, and processes for the production of these preparations.

The active compound(s) can optionally also be present in microencapsulated form in one or more of the excipients indicated above.

The therapeutically active compounds should be present in the pharmaceutical preparations mentioned above in a concentration of approximately 0.1 to 99.5, preferably of approximately 0.5 to 95, % by weight of the total mixture.

Apart from the compounds according to the invention, the abovementioned pharmaceutical preparations can also contain further pharmaceutical active compounds.

In general, it has proved advantageous both in human and in veterinary medicine to administer the active compounds according to the invention in total amounts of from approximately 0.5 to approximately 500, preferably 5 to 100, mg/kg of body weight every 24 hours, if appropriate in the form of several individual doses, to achieve the desired results. An individual dose contains the active compound(s) according to the invention, preferably in amounts of from approximately 1 to approximately 80, in particular 3 to 30, mg/kg of body weight.

For the purpose of widening the spectrum of action and in order to achieve an increase in activity, the compounds according to the invention can also be combined with other antibiotics.

Appendix to the experimental section

List of the eluent mixtures used for chromatography
I Dichloromethane:methanol
II Toluen:ethyl acetate
III Acetonitrile:water
IV Ethyl acetate
V Petroleum ether:ethyl acetate
Abbreviations
Z Benzyloxycarbonyl
Boc tert-Butyloxycarbonyl
DMF Dimethylformamide Ph Phenyl
Me Methyl
THF Tetrahydrofuran
CDI Carbonyldiimidazole
DCE Dichloroethane
Starting compounds

Example I
Methyl 3-amino-6-methyl-thieno[2,3-b]pyridine-2-carboxylate

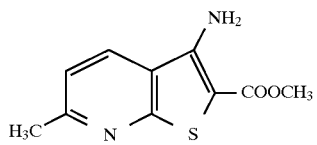

45 g (295 mmol) of 2-chloro-6-methylpyridine-3-carbonitrile are dissolved in 180 ml of DMSO and treated with 90 ml (649 mmol) of triethylamine and 28 ml (310 mmol) of methyl mercaptoacetate, and the mixture is stirred at 80° C. for 18 h. It is allowed to come to room temperature, is tipped onto ice-water, the precipitate is filtered off with suction, and the residue is washed with petroleum ether and dried for 5 h in a recirculating air oven at 60° C.

Yield: 63 g (96%) MS: 222 [$M^{30}$, 100%] $^1$H-NMR ($D_6$-DMSO, TMS): 8.4 (d, J=9 Hz, 1H); 7.83 (d, J=9 Hz, 1H); 7.26 (s, 2H); 3.8 (s, 3H); 2.58 (s, 3H).

Example II
Methyl 3-amino-5-methyl-thieno[2,3-b]pyridine-2-carboxylate

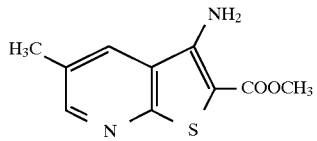

37.5 g (250 mmol) of 2-mercapto-3-cyano-5-methylpyridine are dissolved in 175 ml of DMSO and treated with 76 ml (550 mmol) of triethylamine. 22 ml (250 mmol) of methyl chloroacetate are added dropwise in the course of 5 min to the solution thus obtained. The mixture is stirred for 5 h at 80° C., added to ice-water, and the precipitated solid is filtered off with suction, washed well with diethyl ether and dried in a recirculating air oven at 50° C.

Yield: 53.5 g (96%) MS: 222 [M$^+$, 100%] $^1$H-NMR ($D_6$-DMSO): 8.55 (s, 1H); 8.35 (s, 1H); 7.25 (s, 2H); 3.7 (s, 3H); 2.4 (s, 3H).

Example III
Methyl 6-methyl-thieno[2,3-b]pyridine-2-carboxylate

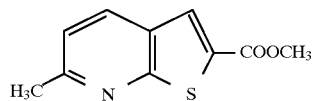

209 ml of water are cautiously mixed with 628 ml of conc. $H_2SO_4$, and the solution is cooled to 0° C. and treated with 62 g (279 mmol) of the compound from Example I. A solution of 61.5 g (894 mmol) of sodium nitrite in 280 ml of water is then added dropwise such that the internal temperature of the reaction solution does not exceed +5° C. After addition is complete, the mixture is stirred at 0° C. for 1 h.

The reaction solution thus obtained is introduced into 1.675 l of 50% strength hypophosphoric acid such that the internal temperature does not climb above +7° C. After addition is complete, the mixture is stirred at 0° C. for 30 min and kept overnight at +4° C. It is then rendered neutral with solid $NaHCO_3$ (foams vigorously) and the precipitated solid is filtered off with suction. The residue is stirred for 10 min in 2 l of acetone, filtered off with suction and dried at 50° C. in a recirculating air oven.

Yield: 24.3 g (42%) MS: 207 [$M^{30}$, 90%] $^1$H-NMR ($D_6$-DMSO, TMS): 8.3 (d, J=9 Hz, 1H); 8.15 (s, 1H); 7.4 (d, J=9 Hz, 1H); 3.9 (d, 3H); 2.63 (s, 3H).

Example IV
6-Methyl-thieno[2,3-b]pyridine-2-carboxylic acid

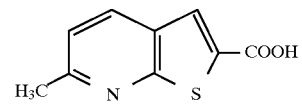

23 g (111 mmol) of the compound from Example III are dissolved in 660 ml of ethanol, treated with 93.5 g (1.66 mol) of potassium hydroxide and heated at reflux for 30 min. After cooling to room temperature, the precipitate is filtered off with suction and washed well with ethanol. The precipitate is dissolved in water and acidified to pH 4 using acetic acid. The precipitated acid is filtered off with suction, washed with 2 l of petroleum ether and dried at 50° C. in a recirculating air cabinet.

Yield: 18.6 g (87%) $^1$H-NMR ($D_6$-DMSO, TMS): 12.1 (s, 1H); 8.28 (d, J=9 Hz, 1H); 8.05 (s, 1H); 7.39 (d, J=9 Hz, 1H); 2.62 (s, 3H).

The compounds shown in Table I are prepared analogously to the procedures for compounds I–IV:

TABLE I

| Ex. No. | $R^{21}$ | $R^{22}$ | Yield (% of theory) | MS | M.p. (°C.) |
|---|---|---|---|---|---|
| V | $CH_3$ | H | 91 | — | 263 dec. |
| VI* | H | H | 86 | 180 [M + H]$^-$ | 312 dec. |

*S. W. Schneller, F. W. Clough, I. E. Hardee, J. Heterocycl. Chem. (1976) 273-5

Example VII
6-Methyl-thieno[2,3-b]pyridine-2-carboxylic acid azide

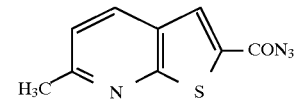

18 g (93.2 mmol) of the compound from Example IV are dissolved in 180 ml of acetone and treated with 15.4 ml (110 mmol) of triethylamine. This reaction mixture is cooled to −15° C. and slowly treated with a solution of 15.4 ml (121 mmol) of isobutyl chloroformate in 77 ml of acetone such that the internal temperature does not exceed −5° C. The mixture is stirred for 2 h at −10° C. and a solution of 9 g (140 mmol) of sodium azide in water is added dropwise, the mixture is stirred for 2 h at 0° C. and tipped onto 2.5 l of ice-water, and the precipitate which is deposited is filtered off with suction, washed well with water and dried in air.

Yield: 18 g (89% of theory)

Example VIII
2-Butyloxycarbonylamino-6-methyl-thieno[2,3-b]pyridine

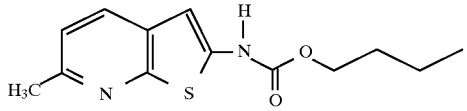

18 g (82 mmol) of the compound from Example VII are introduced in portions into 390 ml of boiling butanol. After addition is complete, the mixture is stirred under reflux for 10 min, cooled to room temperature and concentrated, and the residue is stirred in diethyl ether, filtered off with suction and dried at 50° C. in a recirculating air oven.

Yield: 20.3 g (93%) M.p.: 162° C. $^1$H-NMR (D$_6$-DMSO, TMS): 7.88 (d, J=9 Hz, 1H); 7.24 (d, J=9 Hz, 1H); 6.75 (s, 1H); 4.18 (t, J=7 Hz, 2H); 2.53 (s, 3H); 1.65 (q, J=7 Hz, 2H); 1.39 (h, J=7 Hz, 2H); 0.93 (t, J=7 Hz, 3H).

The compounds shown in Table II are prepared analogously to the procedures for compounds VII and VIII:

TABLE II

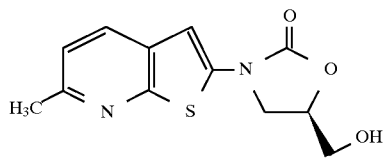

| Ex. No. | R$^{23}$ | R$^{24}$ | Yield (% of theory) | M.p. (°C.) |
|---|---|---|---|---|
| IX | CH$_3$ | H | 84 | 180 |
| X | H | H | 68 | 204 |

PREPARATION EXAMPLES

Example 1
(5R)-3-[6-Methyl-pyrido[2,3-b]thienyl]-5-hydroxymethyl-oxazolidin-2-one

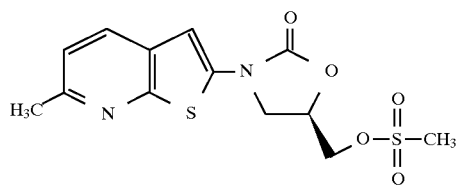

20.3 g (76.8 mmol) of the compound from Example VIII are dissolved in 150 ml of THF, treated with 10 mg of benzylidenebenzylimine and cooled to −70° C. About 31 ml of 2.5N n-butyllithium solution in hexane are then slowly added dropwise until the colour changes to red. 10.9 ml (76.8 mmol) of (R)-glycidyl butyrate are then added dropwise. The mixture is allowed to come to room temperature, and is treated with saturated ammonium chloride solution and stirred for 30 min at room temperature, and the precipitate which is deposited is filtered off with suction. The residue is washed with a little water and with plenty of diethyl ether and dried at 50° C. in a recirculating air oven.

Yield: 19.7 g (97% of theory) M.p.: 245° C. dec. R$_f$: 0.24 (I, 100:5) MS: 265 [(M+H)$^+$, 100%] $^1$H-NMR (D$_6$-DMSO, TMS): 7.95 (d, J=9 Hz, 1H); 7.25 (d, J=9 Hz, 1H); 6.69 (s, 1H); 5.3 (s, 1H); 4.8–4.96 (m, 1H); 4.18 (t, J=9.5 Hz, 1H); 3.93 (dd, J=9.5 Hz, 6.5 Hz, 1H); 3.55–3.8 (m, 2H); 2.55 (s, 3H).

The compounds shown in Table 1 were prepared analogously to compound 1:

TABLE 1

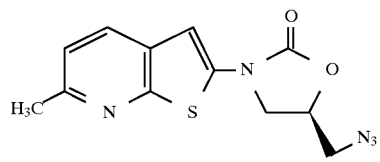

| Ex. No. | R$^{25}$ | R$^{26}$ | Yield (% of theory) | MS | M.p. (°C.) |
|---|---|---|---|---|---|
| 2 | CH$_3$ | H | 88 | — | 245 dec. |
| 3 | H | H | 98 | 251 [M + H]$^-$; 100% | 235 dec. |

Example 4
(5R)-3-[6-Methyl-pyrido[2,3-b]thienyl]-5-methanesulphonyloxymethyl-oxazolidin-2-one A solution of 18.8 g (71 mmol) of the compound from Example 1 in 290 ml of pyridine is cooled to 0° C. and slowly treated with 11 ml (142 mmol) of methanesulphonyl chloride. The mixture is kept at 4° C. for 16 h and concentrated. The residue is stirred into 5% strength sodium hydrogen carbonate solution, filtered off with suction and washed with water and diethyl ether and dried at 50° C. in a recirculating air oven.

Yield: 23 g (95% of theory) R$_f$=0.47 (I, 100:5)

Example 5
(5R)-3-[6-Methyl-pyrido[2,3-b]thienyl]-5-azido-methyl-oxazolidin-2-one 23 g (67.1 mmol) of the compound from Example 4 are dissolved in 160 ml of DMF and treated with 4.8 g (74 mmol) of sodium azide. The reaction mixture thus obtained is stirred at 70° C. for 16 h. It is allowed to cool to room temperature and is tipped onto 2 l of ice-water. The precipitated solid is filtered off with suction, washed with water and petroleum ether and dried in air.

Yield: 17.9 g (92% of theory) R$_f$: 0.31 (I, 100:2) M.p.: 181° C. dec. MS: 290 [(M+H)$^{31}$, 100%] $^1$H-NMR (D$_6$-DMSO,TMS): 7.96 (d, J) 9 Hz, 1H); 7.75 (d, J=9 Hz, 1H); 6.72 (s, 1H); 4.98–5.12 (m, 1H); 4.24 (t, J=9.5 Hz, 1H); 3.78–3.9 (m, 3H); 2.55 (s, 3H).

The compounds shown in Table 2 are prepared analogously to the procedures for Examples 4 and 5:

TABLE 2

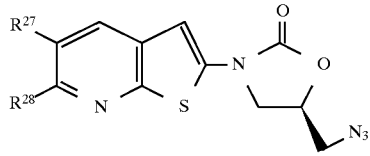

| Ex. No. | $R^{27}$ | $R^{28}$ | Yield (% of theory) | MS | M.p. (°C.) |
|---|---|---|---|---|---|
| 6 | $CH_3$ | H | 95 | 289 [M⁻] | 204 dec. |
| 7 | H | H | 54 | — | 197 dec. |

Example 8

(5S)-3-[6-Methyl-pyrido[2,3-b]thienyl]-5-aminomethyl-oxazolidin-2-one hydrochloride

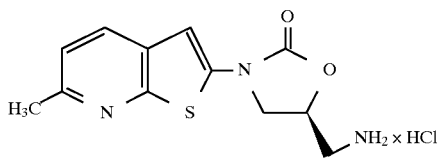

5 g (17.3 mmol) of the compound from Example 5 are dissolved in 400 ml of ethanol, treated with 500 mg of 5% strength palladium on active carbon and hydrogenated under a hydrogen pressure of 3 bar for 16 h. The catalyst is filtered off, the solution is concentrated, the residue is taken up in methylene chloride and the solution is treated slowly with 5 ml of 4.5N HCl in ether. The mixture is stirred at room temperature for 1 h, and the solid is filtered off with suction and washed with ether. The residue is dried at 40° C. in a recirculating air oven.

Yield: 5.74 g (98% of theory) $^1$H-NMR ($D_2O$): 8.3 (d, J=9 Hz, 1H); 7.5 (d, J=9 Hz, 1H); 6.78 (s, 1H); 5.11–5.27 (m, 1H); 4.37 (t, J=9.5 Hz, 1H); 3.95 (dd, J=9.5 Hz, J=6.5 Hz, 1H); 3.30–3.5 (m, 2H); 2.65 (s, 3H).

The compounds shown in Table 3 are prepared analogously to compound 8:

TABLE 3

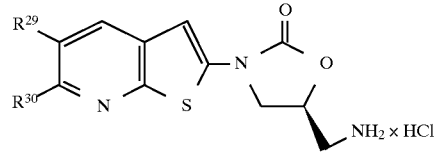

| Ex. No. | $R^{29}$ | $R^{30}$ | Yield (% of theory) | MS | M.p. (°C.) |
|---|---|---|---|---|---|
| 9 | $CH_3$ | H | 68 | 363 ([M + H]⁻; 40%) | — |
| 10 | H | H | 81 | 249 ([M⁻]; 60%) | 257 u.Z. |

Example 11

(5S)-3-[6-Methyl-pyrido[2,3-b]thienyl]-5-acetylaminomethyl-oxazolidin-2-one

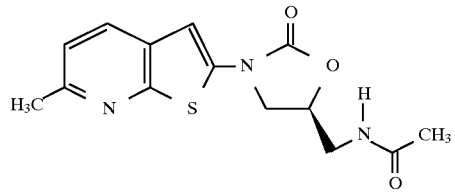

1.5 g (4.1 mmol) of the compound from Example 8 are treated with 1.14 ml (8.2 mmol) of triethylamine and dissolved in 8 ml of pyridine. The reaction solution is cooled to 0° C. and 0.73 ml (10.2 mmol) of acetyl chloride are added dropwise. After 4 hours at 0° C., the mixture is treated with 1 ml of methanol, concentrated and chromatographed on silica gel (methylene chloride:methanol=100.3).

Yield: 0.84 g (67%) M.p.: 215° C. dec. $R_f$: 0.44 (I; 10.1) MS: 306 [(M+H)⁺; 100%] $^1$H-NMR ($D_6$-DMSO, TMS): 8.3 (t, J=6.5 Hz, 1H); 7.95 (d, J=9 H, 1H); 7.25 (d, J=9 Hz, 1H); 6.68 (s, 1H); 4.83–4.98 (m, 1H); 4.2 (t, J=9.5 Hz, 1H); 3.83 (dd, J=9.5 Hz, J=6.5 Hz, 1H); 3.47 (t, J=6 Hz, 2H); 2.55 (s, 3H); 1.85 (s, 3H).

Example 12

(5S)-3-[6-Methyl-pyrido[2,3-b]thienyl]-5-thioacetylaminomethyl-oxazolidin-2-one

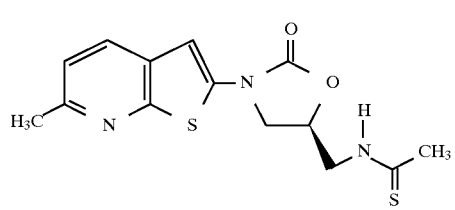

673 mg (2 mmol) of the compound from Example 8 are dissolved in 4 ml of THF, and the solution is treated with 0.61 ml (4.4 mmol) of triethylamine and 0.26 ml (2.2 mmol) of ethyl dithioacetate and stirred at room temperature for 18 h. It is concentrated and the residue is chromatographed on silica gel (methylene chloride:methanol=100:1).

Yield: 475 mg (74%) M.p.: 202 dec. $R_f$: 0.3 (I; 100:5) MS: 321 ($M^{30}$, 20%) $^1$H-NMR ($D_6$-DMSO, TMS): 10.45 (s, 1H); 7.95 (d, J=9 Hz, 1H); 7.25 (d, J=9 Hz, 1H); 6.68 (s, 1H); 5.05–5.2 (m, 1H); 4.25 (t, J=9.5 Hz, 1H); 3.98 (t, J=6.5 Hz, 2H); 3.9 (dd, J=9.5 Hz, J=6.5 Hz, 1H); 2.55 (s, 3H); 2.43 (s, 3H).

The compounds shown in Table 4 were prepared analogously to the procedures of Examples 11 and 12:

TABLE 4

[Structure: pyridothienyl-oxazolidinone with R31, R32 substituents and R33 group on terminal NH]

| Ex. No. | R31 | R32 | Acetylating agent | R33 | Equivalents Et₃N | Yield (% of theory) | MS | M.p. (°C.) | R_f (eluent mixture; ratio) |
|---|---|---|---|---|---|---|---|---|---|
| 13 | CH₃ | H | CH₃COCl | CH₃—C(=O)— | 2.3 | 46 | 306 [M + H]⁺; 100% | 221 dec. | 0.23 [1; 100:5] |
| 14 | H | H | CH₃COCl | CH₃—C(=O)— | 2.3 | 45 | 291 [M]⁺; 100% | 220 dec. | 0.25 [1; 100:5] |
| 15 | H | H | CH₃NCS | CH₃—NH—C(=S)— | 3 | 54 | 323 [M + H]⁺; 10% | 148 dec. | 0.25 [1; 100:5] |
| 16 | H | H | CH₃CSSCH₂CH₃ | CH₃—C(=S)— | 2 | 66 | 308 M + H]⁺; 50% | 190 dec. | 0.30 [1; 100:5] |
| 17 | H | CH₃ | CH₃NCS | CH₃—NH—C(=S)— | 3 | 70 | 337 [M + H]⁺; 10% | 178 dec. | 0.14 [1; 100:5] |
| 18 | CH₃ | H | CH₃NCS | CH₃—NH—C(=S)— | 3 | 40 | 337 [M + H]⁺; 30% | 167 dec. | 0.27 [1; 100:5] |
| 19 | CH₃ | H | CH₃CSSCH₂CH₃ | CH₃—C(=S)— | 2 | 39 | 321 [M]⁺, 10% | 186 dec. | 0.37 [1; 100:5] |
| 20 | H | CH₃ | CH₂CH₂COCl | CH₃—CH₂—C(=O)— | 3 | 25 | 320 [M + H]⁺ 100% | 222 dec. | 0.26 (1; 100:5) |
| 21 | H | CH₃ | cyclopropyl-COCl | cyclopropyl-C(=O)— | 3 | 46 | 322 [M + H]⁺ 100% | 228 dec. | 0.26 (1; 100:5) |
| 22 | H | CH₃ | CH₃O—C(=O)—Cl | CH₃O—C(=O)— | 3 | 47 | 322 [M + H]⁺ 100% | 227 dec. | 0.34 (1; 100:5) |

We claim:

1. A pyrido-fused thienyl- or furanyl-oxazolidinone compound of the formula (I):

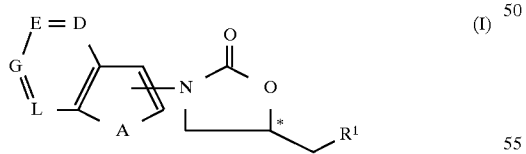

in which
A represents an oxygen or sulfur atom or the —SO₂— group;
one of D, E, G and L represents a nitrogen atom and three of D, E, G and L represent a CR² group;
in which
R² represents hydrogen, cyano, nitro, carboxyl, straight-chain or branched alkyl, acyl or alkoxy each having up to 7 carbon atoms, halogen, —NR³R⁴, —CO—NR⁵R⁶, —NR⁷—CO—R⁸ or —S(O)$_a$R⁹;
in which
R³, R⁴, R⁵, R⁶, R⁷ and R⁸ are independently represent hydrogen, phenyl or straight-chain or branched alkyl having up to 6 carbon atoms;
a represents a number 0, 1 or 2;
R⁹ represents phenyl or straight-chain or branched alkyl having up to 4 carbon atoms;
R¹ represents azido, hydroxyl, —OR¹⁰, —O—SO₂R¹¹ or —NR¹²R¹³,
in which
R¹⁰ represents straight-chain or branched acyl having up to 8 carbon atoms or a hydroxyl protective group;
R¹¹ represents straight-chain or branched alkyl having up to 4 carbon atoms or phenyl which is optionally substituted by straight-chain or branched alkyl having up to 4 carbon atoms;
R¹² and R¹³ independently represent cycloalkyl having 3 to 6 carbon atoms, hydrogen, phenyl or straight-chain or branched alkyl or alkoxy each having up to 8 carbon atoms or an amino protective group; or
R¹² or R¹³ represents —CO—R¹⁴, —CS—R¹⁴', —P(O)(OR¹⁵)(OR¹⁶) or —SO₂—R¹⁷;

in which
- $R^{14}$ and $R^{14'}$ independently represent cycloalkyl having 3 to 6 carbon atoms, trifluoromethyl, straight-chain or branched alkoxy having up to 8 carbon atoms, phenyl, benzyloxy or hydrogen; or represent straight-chain or branched alkyl having up to 8 carbon atoms, which is optionally substituted by cyano, halogen or trifluoromethyl; or represent straight-chain or branched alkylthio or acyl each having up to 6 carbon atoms; or represent —$NR^{18}R^{19}$;
  in which
  - $R^{18}$ and $R^{19}$ independently represent hydrogen, phenyl or straight-chain or branched alkyl having up to 6 carbon atoms; or represent a 5-membered aromatic heterocycle having up to 3 heteroatoms independently selected from the group consisting of S, N and O;
- $R^{15}$ and $R^{16}$ independently represent hydrogen or straight-chain or branched alkyl having up to 4 carbon atoms; and
- $R^{17}$ represents straight-chain or branched alkyl having up to 4 carbon atoms or phenyl;

said compound being a pure stereoisomer or a stereoisomer mixture;

or a salt of said compound.

2. A compound according to claim 1,
in which
A represents an oxygen or sulfur atom or the —$SO_2$— group;
one of D, E, G and L represents a nitrogen atom and three of D, E, G and L represent a $CR^2$ group;
in which
$R^2$ represents hydrogen, straight-chain or branched alkyl having up to 6 carbon atoms, fluorine, chlorine or bromine;
$R^1$ represents azido, hydroxyl, —$OR^{10}$, —O—$SO_2R^{11}$ or —$NR^{12}R^{13}$;
in which
$R^{10}$ represents straight-chain or branched acyl having up to 6 carbon atoms or benzyl;
$R^{11}$ represents straight-chain or branched alkyl having up to 3 carbon atoms, phenyl or tolyl;
$R^{12}$ and $R^{13}$ independently represent cyclopropyl, cyclopentyl, cyclohexyl, hydrogen, phenyl or straight-chain or branched alkyl or alkoxy each having up to 6 carbon atoms, tert-butoxycarbonyl or benzyloxycarbonyl; or
$R^{12}$ or $R^{13}$ represents —CO—$R^{14}$, —CS—$R^{14'}$, —P(O)($OR^{15}$)($OR^{16}$) or —$SO_2$—$R^{17}$;
in which
$R^{14}$ and $R^{14'}$ independently represent cyclopropyl, cyclobutyl, cyclopentyl, cyclohexyl, trifluoromethyl, straight-chain or branched alkoxy having up to 6 carbon atoms, phenyl, benzyloxy or hydrogen; or
represent straight-chain or branched alkyl having up to 6 carbon atoms, which is optionally substituted by cyano, fluorine, chlorine, bromine or trifluoromethyl; or
represent straight-chain or branched alkylthio or acyl each having up to 5 carbon atoms; or
represent —$NR^{18}R^{19}$;
in which
$R^{18}$ and $R^{19}$ independently represent hydrogen, phenyl or straight-chain or branched alkyl having up to 4 carbon atoms; or
represent isoxazolyl, furyl, thienyl, pyrryl, oxazolyl or imidazolyl;
$R^{15}$ and $R^{16}$ independently represent hydrogen or straight-chain or branched alkyl having up to 3 carbon atoms; and
$R^{17}$ represents straight-chain or branched alkyl having up to 3 carbon atoms or phenyl;

said compound being a pure stereoisomer or a stereoisomer mixture;

or a salt of said compound.

3. A compound according to claim 1,
in which
A represents an oxygen or sulfur atom or the —$SO_2$— group;
one of D, E, G and L represents a nitrogen atom and three of D, E, G and L represent a $CR^2$ group;
in which
$R^2$ represents hydrogen, straight-chain or branched alkyl having up to 3 carbon atoms or fluorine;
$R^1$ represents azido, hydroxyl, —$OR^{10}$, —O—$SO_2R^{11}$ or —$NR^{12}R^{13}$;
in which
$R^{10}$ represents straight-chain or branched acyl having up to 5 carbon atoms or benzyl;
$R^{11}$ represents methyl, ethyl, phenyl or tolyl;
$R^{12}$ and $R^{13}$ independently represent cyclopropyl, cyclopentyl, cyclohexyl, hydrogen, phenyl or straight-chain or branched alkyl or alkoxy each having up to 5 carbon atoms, tert-butoxycarbonyl or benzyloxycarbonyl; or
$R^{12}$ or $R^{13}$ represents —CO—$R^{14}$, —CS—$R^{14'}$, —P(O)($OR^{15}$)($OR^{16}$) or —$SO_2$—$R^{17}$;
in which
$R^{14}$ and $R^{14'}$ independently represent cyclopropyl, cyclobutyl, cyclopentyl, cyclohexyl, trifluoromethyl, straight-chain or branched alkoxy having up to 5 carbon atoms, phenyl, benzyloxy or hydrogen; or
represent straight-chain or branched alkyl having up to 5 carbon atoms, which is optionally substituted by cyano, fluorine, chlorine, bromine or trifluoromethyl; or
represent straight-chain or branched alkylthio or acyl each having up to 4 carbon atoms; or
represent —$NR^{18}R^{19}$;
in which
$R^{18}$ and $R^{19}$ independently represent hydrogen, phenyl or straight-chain or branched alkyl having up to 3 carbon atoms; or
represent isoxazolyl, furyl, oxazolyl or imidazolyl;
$R^{15}$ and $R^{16}$ independently represent hydrogen, methyl or ethyl; and
$R^{17}$ represents methyl or phenyl;

said compound being a pure stereoisomer or a stereoisomer mixture;

or a salt of said compound.

4. A compound according to claim 1, which has the formula:

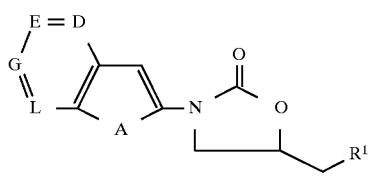

said compound being a pure stereoisomer or a stereoisomer mixture;
or a salt of said compound.

5. A compound according to claim 1, which is selected from the group consisting of (5S)-3-[6-methyl-pyrido[2,3-b]thienyl]-5-thioacetylaminomethyl-oxazolidin-2-one, (5S)-3[5-methyl-pyrido[2,3-b]thienyl]-5-acetylaminomethyl-oxazolidin-2-one, (5S)-3-[pyrido[2,3-b]thien-2-yl]-5-thioacetylaminomethyl-oxazolidin-2-one, 1-methyl-3-(2-oxo-3-[5-(5S)-methyl-thieno[2,3-b]pyridin-2-yl]-oxazolidin-5-ylmethyl)-thiourea and (5S)-3-[5-methyl-pyrido[2,3-b]-thienyl]-5-thioacetylaminomethyl-oxazolidin-2-one.

6. A pharmaceutical composition which comprises a compound according to claim 1 or a salt thereof and an inert carrier.

7. A method of treating infections caused by bacteria or bacteria-like microorganisms in a human or animal in need thereof which comprises administering an effective amount therefor of a compound according to claim 1 or salt thereof to said human or animal.

8. A process for the preparation of a compound of the formula (I) according to claim 1, comprising:

a) reacting a compound of the formula (II) or (III):

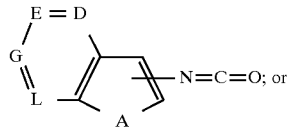 (II)

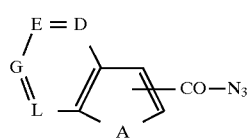 (III)

in which

A, D, E, G and L have the meanings indicated in claim 1, with lithium bromide/$(C_4C_9)_3P(O)$ and an epoxide of the formula (IV):

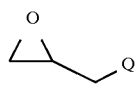 (IV)

in which

Q represents $C_1$-$C_6$-acyloxy;

in an inert solvent and, optionally, in the presence of a base, and, if $R^1$=OH, hydrolyzed or transesterified to liberate the hydroxyl function, or b) reacting a compound of the formula (V):

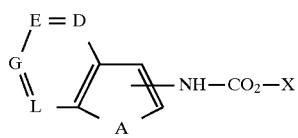 (V)

in which

A, D, E, G and L have the meaning indicated above, and

X represents a protective group, with an epoxide of the formula (IV) in an inert solvent and in the presence of a base;

or c) if $R^1$=OH, converting a compound of the formula (III) by elimination of nitrogen in an alcohol into a compound of the formula (Va):

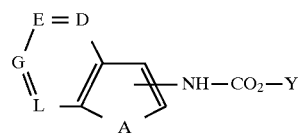 (Va)

in which

A, D, E, G and L have the meaning indicated above, and

Y represents straight-chain or branched $C_2$-$C_6$-alkyl, and reacting the compound of formula (Va) with an epoxide of the formula (IV) in an inert solvent and in the presence of a base, of d) reacting a compound of the formula (VI):

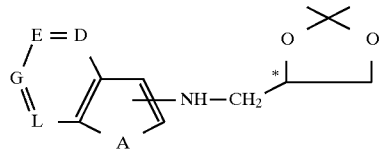 (VI)

in which

A, D, E, G and L have the meaning indicated above, with an acid and diethyl carbonate to yield the compound of formula (I) directly, or first a compound of formula (VII):

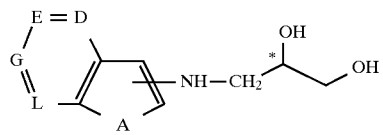 (VII)

in which

A, D, E, G and L have the meaning indicated above, which is then cyclized in an inert solvent in the presence of an auxiliary, or e) reacting a compound of the formula (Ia):

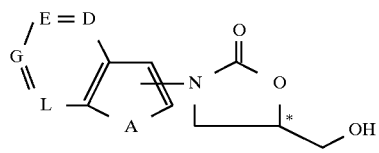 (Ia)

in which

A, D, E, G and L have the meaning indicated above, with optionally substituted ($C_1$-$C_4$)-alkyl- or phenylsulfonyl chlorides in an inert solvent and in the presence of a base to yield the compound of the formula (Ib):

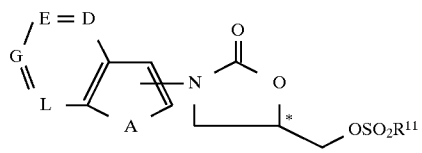

in which

A, D, E, G and L above, and have the meaning indicated above, and $R^{11}$ has the meaning indicated in claim 1, then reacting the compound of formula (Ib) with sodium azide in an inert solvent to yield an azide of the formula (Ic):

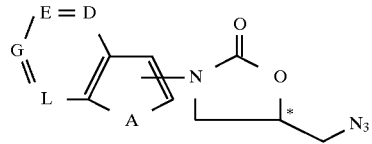

in which

A, D, E, G and L have the meaning indicated above, then reacting the compound of formula (Ic) with ($C_1$-$C_4$-O)$_3$-P or PPh$_3$ and with an acid in an inert solvent to yield the amine of the formula (Id):

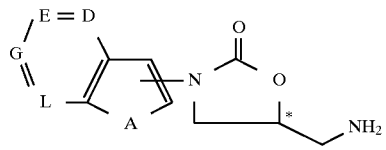

in which

A, D, E, G and L have the meaning indicated above, and then reacting the compound of formula (Id) with acetic anhydride or an acylating agent of the formula (VIII):

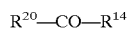

in which $R^{14}$ has the meaning indicated in claim 1, and $R^{20}$ represents halogen or the radical —OCOR$^{14}$, in an inert solvent to yield the compound of the formula (Ie):

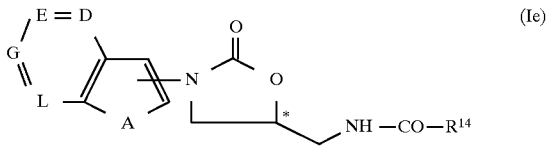

in which

A, D, E, G, L and $R^{14}$ have the meaning indicated above, and optionally reacting a compound of the formula (Id) with ethyl dithiocarboxylate and triethylamine to yield a compound of formula (I) wherein $R^1$ represents —NR$^{12}$—CS—R$^{14}$, and with thioisocyanate to yield a compound of formula (I) wherein $R^1$ represents —NR$^{12}$—CS=NR$^{18}$R$^{19}$, and optionally oxidizing a compound of formula (I) wherein A represents —S— to yield a compound of formula (I) wherein A represents —SO$_2$—, and optionally separating individual stereoisomers.

\* \* \* \* \*

UNITED STATES PATENT AND TRADEMARK OFFICE
CERTIFICATE OF CORRECTION

PATENT NO. : 5,827,857
DATED : October 27, 1998
INVENTOR(S) : Bernd Riedl, et al.

It is certified that error appears in the above-indentified patent and that said Letters Patent is hereby corrected as shown below:

Col. 28, Line 31

After "a base" and before "d) reacting" delete "of" and substitute --or--

Signed and Sealed this

Twenty-sixth Day of October, 1999

Attest:

Q. TODD DICKINSON

Attesting Officer

Acting Commissioner of Patents and Trademarks